(12) United States Patent
Neev

(10) Patent No.: US 6,402,739 B1
(45) Date of Patent: Jun. 11, 2002

(54) ENERGY APPLICATION WITH COOLING

(75) Inventor: Joseph Neev, Lake Forest, CA (US)

(73) Assignee: Y-Beam Technologies, Inc., Lake Forest, CA (US)

(*) Notice: Subject to any disclaimer, the term of this patent is extended or adjusted under 35 U.S.C. 154(b) by 0 days.

(21) Appl. No.: 09/449,888

(22) Filed: Nov. 30, 1999

Related U.S. Application Data (60) Provisional application No. 60/111,436, filed on Dec. 8, 1998.

(51) Int. Cl.[7] .................................................. A61B 18/18
(52) U.S. Cl. .......................... 606/9; 606/13; 606/23; 606/27; 606/33; 607/88; 607/96
(58) Field of Search ................... 606/2, 3, 7–9, 606/10, 12, 20, 22–25, 27; 607/88, 89, 96, 100, 101; 128/898

(56) References Cited

U.S. PATENT DOCUMENTS

| | | | | | |
|---|---|---|---|---|---|
| 5,207,670 A | * | 5/1993 | Sinofsky | .................... | 606/8 |
| 5,409,479 A | * | 4/1995 | Dew et al. | .................... | 606/9 |
| 5,486,172 A | * | 1/1996 | Chess | .................... | 606/2 |
| 5,683,380 A | * | 11/1997 | Eckhouse et al. | .................... | 606/9 |
| 5,735,844 A | * | 4/1998 | Anderson et al. | .................... | 606/8 |
| 5,810,801 A | * | 9/1998 | Anderson et al. | .................... | 606/9 |
| 5,814,040 A | * | 9/1998 | Nelson et al. | .................... | 606/9 |
| 5,820,626 A | * | 10/1998 | Baumgardner | .................... | 606/132 |
| 5,830,208 A | * | 11/1998 | Muller | .................... | 606/9 |
| 5,879,346 A | * | 3/1999 | Waldman et al. | .................... | 606/9 |
| 6,162,211 A | * | 12/2000 | Tankovich et al. | .................... | 606/9 |
| 6,221,068 B1 | * | 4/2001 | Fried et al. | .................... | 606/8 |
| 6,251,100 B1 | * | 6/2001 | Flock et al. | .................... | 606/2 |

* cited by examiner

Primary Examiner—Linda C. M. Dvorak
Assistant Examiner—Ahmed Farah
(74) Attorney, Agent, or Firm—Price and Gess (57) ABSTRACT

A method for applying energy to biological tissue. An electromagnetic energy source is directed to apply the energy to a region of the tissue, so as to ablate a portion of the tissue in the region. Preferably, cooling of tissue in the region is initiated subsequent to the ablation.

5 Claims, 8 Drawing Sheets

ENERGY APPLICATION WITH COOLING

CROSS-REFERENCE TO RELATED APPLICATION

This application claims priority from U.S. provisional patent application No. 60/111,436, entitled, "A method and apparatus for surgery and material processing," filed Dec. 8, 1998, which is assigned to the assignee of the present patent application and incorporated herein by reference.

FIELD OF THE INVENTION

The present invention relates generally to the application of energy to biological tissue, and specifically to the application of electromagnetic energy to the skin.

BACKGROUND OF THE INVENTION

It is known in the art to apply electromagnetic energy to biological tissue to engender changes therein. Sunbathers, for example, regularly expose themselves to bright sunlight in order to increase melanocyte activity in the basal layer of the epidermis, responsive to the sun's ultraviolet (UV) radiation. Artificial UV sources have been created to satisfy the desire for a "healthy" looking tan in the winter. Other forms of electromagnetic energy, laser-light in particular, are currently used in a large range of therapeutic and cosmetic procedures, including eye surgery, hair removal, wrinkle removal, and tattoo removal.

PCT publication WO 98/55035, which is incorporated herein by reference, describes methods for minimizing injury to biological tissue surrounding a site exposed to pulses of electromagnetic energy.

U.S. Pat. No. 5,752,949 to Tankovich et al., which is incorporated herein by reference, describes a hair-removal method for placing a contaminant in the skin, using a laser to create explosions to drive the contaminant deep into hair ducts in the skin, and subsequently heating the contaminant to kill biological tissue surrounding the contaminant. The rate of application of energy is controlled to allow cooling of the skin.

U.S. Pat. No. 5,814,040 to Nelson et al., which is also incorporated herein by reference, describes a method for port wine stain removal, including applying a coolant to the skin, and subsequently directing laser radiation below the cooled area.

U.S. Pat. 5,810,801 to Anderson et al., which is also incorporated herein by reference, describes a method for treating wrinkles in the skin, including directing electromagnetic energy to a target region of the skin, while cooling an area above the target region.

SUMMARY OF THE INVENTION

It is an object of some aspects of the present invention to provide improved apparatus and methods for applying energy to a material.

It is another object of some aspects of the present invention to provide improved apparatus and methods for removing heat generated during application of electromagnetic energy to a material.

It is a further object of some aspects of the present invention to provide improved apparatus and methods for removing heat generated during application of electromagnetic energy to biological tissue.

It is still a further object of some aspects of the present invention to provide improved apparatus and methods for decreasing pain during application of electromagnetic energy to biological tissue.

It is yet a further object of some aspects of the present invention to provide improved apparatus and methods for performing medical treatments.

It is also an object of some aspects of the present invention to provide improved apparatus and methods for performing cosmetic treatments.

It is further an object of some aspects of the present invention to provide improved apparatus and methods for enabling a visible wavelength electromagnetic energy source to perform material and tissue removal and modification.

It is yet a further object of some aspects of the present invention to provide methods and apparatus for enabling a visible wavelength low-power electromagnetic energy source to perform material and tissue removal and modification.

It is still a further object of some aspects of the present invention to provide methods and apparatus for enabling a low-power electromagnetic energy source to perform material and tissue removal and modification.

It is also an object of some aspects of the present invention to provide improved methods and apparatus for enabling a low-power electromagnetic energy source to perform tissue removal and modification, substantially without pain, while controlling the amount of damage to remaining tissue.

In preferred embodiments of the present invention, an energy source applies electromagnetic energy to tissue of a subject, preferably so as to ablate a portion thereof. Thereafter, some of the heat generated by the interaction of the energy with the tissue is removed, typically by applying a coolant or a cooling element to the tissue. Removal of the heat immediately following the application of the energy generally reduces the subject's sensation of the heat, and, in particular, reduces any sensation of pain. Moreover, heat removal typically reduces or eliminates collateral injury to tissue surrounding the ablated area. Typically, although not necessarily, the tissue comprises the subject's skin.

It is known in the art to cool tissue prior to or during the application of electromagnetic energy to a subject's skin. U.S. Pat No. 5,814,040 cited above, for example, describes cooling the epidermis prior to heating tissue thereunder, to minimize damage to the cooled tissue. Similarly, U.S. Pat No. 5,810,801 describes cooling a first region of tissue while heating a second region of tissue thermally coupled thereto. These embodiments of the present invention, by contrast, teach that cooling the tissue following the application of electromagnetic energy is generally advantageous. Furthermore, it is believed that very rapid heating of a target area of the skin, substantially unmitigated by any prior cooling thereof, produces therapeutic results that are superior to techniques which cool a mass of tissue and then apply energy to a cooled target area. In particular, it is believed that the prior art methods which describe cooling of an upper tissue layer prior to interaction of electromagnetic energy therewith generally have an adverse effect on modification and/or ablation of tissue in the upper layer. Notably unlike techniques as taught according to preferred embodiments of the present invention, these prior art methods generally are painful in the absence of an administered anesthetic.

In some preferred embodiments of the present invention, the energy source comprises a laser, whose beam is moved in a pattern over a target area of the skin. The pattern is made up of a sequence of passes over the tissue, each pass describing a line or curve over a predetermined portion of the target area. Typically, the pattern is chosen such that each pass is relatively distant from the preceding one, so that it generally does not cause additional heating of tissue indirectly heated by energy from the preceding pass. The temperature of this latter tissue decreases during the succeeding pass, preferably to approximately the same temperature as prior to the preceding pass. In some of these preferred embodiments, the laser energy is applied to the skin in sets of passes, whereby a set of one or more consecutive passes of the laser across the skin is relatively distant from a preceding set of one or more consecutive passes. The pattern is designed as necessary to ablate tissue, but minimize the undesired accumulation of heat in nearby tissue. Preferably, utilization of a beam pattern as described reduces sensations of pain, and also reduces injury of non-targeted tissue. In some of these embodiments, the tissue is actively cooled, preceding and/or following application of the energy thereto.

In some preferred embodiments of the present invention, a cover is placed over the target area, and the electromagnetic energy is applied through a window in the cover. Preferably, the cover enables an operator to maintain an ambient environment over the target area having properties, such as temperature, pressure, and humidity, which are set so as to minimize pain or discomfort during a procedure. Typically, sensors are coupled to the cover in order to determine parameters of the ambient environment and to generate signals responsive thereto. A control unit is preferably coupled to receive the signals and to actuate various devices so as to cause the signals to converge to desired values. The devices may include, for example, heating and cooling elements, pressure and humidity controllers, and a substance-delivery system. In a preferred embodiment, a temperature sensor monitors skin temperature, and active heating (e.g., using a laser) and cooling are applied as appropriate to keep the skin temperature within predetermined limits.

In a preferred embodiment of the present invention, the target area comprises two or more zones, typically concentrically-arranged, and the electromagnetic energy source applies a different amount of energy to one of the zones from the amount applied to a second one of the zones. Preferably, the highest quantity of energy is applied to the innermost of the concentric zones, and successively smaller quantities of energy are applied to the other zones, responsive to their distance from the innermost zone. In this manner, a smooth transition is obtained from the target area to tissue or material surrounding the target area. By contrast, it is known in the art to use chemical or laser treatments for cosmetic purposes, such as wrinkle removal, but these treatments are typically disadvantageous, in that they often leave a region which clearly appears to have been treated, adjacent to a second region, which clearly has not been treated. For example, when these prior art methods are practiced to achieve wrinkle removal in the mustache area, a patch of generally wrinkle-free skin may be produced, but the patch is often sharply delineated from its neighboring, still-wrinkled skin.

In another preferred embodiment of the present invention, the target area comprises skin, and application of the energy thereto causes pores in the skin to expand. Pore expansion may be used to enhance transdermal drug delivery and/or as part of an acne treatment. Alternatively, drug delivery and acne treatment are performed responsive to the skin's ablation, irrespective of any pore expansion that may occur.

In some preferred embodiments of the present invention, a high absorption substance (HAS) is applied to the target area prior to activation of the electromagnetic energy source, so as to increase the absorption of energy in the target area.

There is therefore provided, in accordance with a preferred embodiment of the present invention, a method for applying energy to biological tissue, including:

directing an electromagnetic energy source to apply the energy to a region of the tissue, so as to ablate a portion of the tissue in the region; and initiating cooling of tissue in the region subsequent to the ablation.

In a preferred embodiment, initiating cooling includes thermoelectrically cooling.

In a preferred embodiment, the method includes applying to the tissue gaseous oxygen at a concentration above 22% by volume to enhance healing of the tissue. Alternatively or additionally, an oxygen-rich solution is applied to the tissue to enhance healing of the tissue. Further alternatively or additionally, a nutrient is applied to the tissue.

Preferably, directing the energy source to apply the energy includes generating a beam of energy having a diameter less than about 250 microns. Further preferably, directing the energy source to apply the energy includes generating a beam of energy having a dwell time over a point in the region of less than 25 ms.

In a preferred embodiment, the tissue includes a varix. Alternatively, the tissue includes tumorous tissue.

In a preferred embodiment, initiating cooling includes applying a cooled surface to the tissue. Preferably, applying the cooled surface includes applying a cooled oscillating member to the tissue, which member is in contact with the tissue during a first phase of its oscillation and is not in contact with the tissue during a second phase of its oscillation.

Preferably, initiating cooling includes applying a coolant. Further preferably, the coolant includes a liquid and the method includes directing a flow of a gas towards a site on the tissue having the liquid applied thereto, so as to increase a rate of evaporation of the liquid.

In a preferred embodiment, the region includes a first region, and initiating cooling includes initiating cooling of tissue in the first region, wherein the method includes terminating cooling of the tissue in the first region subsequent to initiating the cooling thereof, and wherein the method includes directing the source to apply energy to a second region of the tissue so as to ablate a portion of the tissue in the second region subsequent to the initiation of cooling of the tissue in the first region. Alternatively or additionally, directing the source to apply the energy to the second region includes directing the source prior to the termination of the cooling of the tissue in the first region.

In a preferred embodiment, the region includes a first region, and ablating the portion includes ablating tissue to a first ablation depth in the first region. In this embodiment, the method includes directing the electromagnetic energy source to apply energy to a second region of the tissue adjacent to the first region, so as to ablate tissue in the second region to a second ablation depth, smaller than the first ablation depth. Typically, directing the source to apply energy to the second region includes smoothing the appearance of a border region between the first region and an untreated region of the tissue.

Preferably, the tissue includes skin, and the energy is applied so as to reduce a wrinkle in the skin and/or to decrease the size of a skin lesion. Alternatively or additionally, applying the energy includes expanding a pore of the skin, and, optionally, delivering a pharmaceutical product through the expanded pore.

In a preferred embodiment, the method includes applying a pharmaceutical product to the tissue. Typically, applying the product includes applying an anesthetic and/or an antibiotic.

Preferably, applying the energy to the region of the tissue includes placing a material on the tissue to increase the absorption into the tissue of energy applied by the source. Further preferably, the material includes a substance characterized by high absorbency of energy of a wavelength generated by the source. Still further preferably, the energy source includes a CO2 laser. Alternatively or additionally, the output of the energy source is less than about 5 W.

In a preferred embodiment, the electromagnetic energy source includes a broadband emission lamp. Alternatively or additionally, the electromagnetic energy source includes a laser, typically a CO2 laser, an Er:YAG laser, a microchip laser, and/or a diode laser. Preferably, the diode laser has a power output of less than about 500 mW.

Preferably, the method includes actively warming tissue cooled responsive to the cooling, so as to decrease injury of the cooled tissue. Typically, warming includes sensing a temperature of the tissue and warming the tissue responsive thereto. In a preferred embodiment, warming includes applying a heated gas to the tissue. Alternatively or additionally, warming the tissue includes thermoelectrically warming the tissue, and initiating cooling includes thermoelectrically cooling the tissue. Further alternatively or additionally, warming includes applying a heated surface to the tissue. In a preferred embodiment, warming the tissue includes directing the energy source to apply additional energy to the cooled tissue, which additional energy substantially does not cause ablation. Typically, applying the additional energy includes enlarging a beam diameter of the energy source from a first diameter, used for ablating tissue, to a second diameter, used for warming tissue.

There is further provided, in accordance with a preferred embodiment of the present invention, a method for applying energy to biological tissue, including:

directin an electromagnetic energy source to apply energy along a first path on the tissue, so as to ablate tissue in the path;

directing the source to apply energy along a second path on the tissue, relatively distant from the first path, so as to ablate tissue in the second path, while allowing cooling of tissue adjacent to the first path heated by diffusion due to applying the energy to the first path; and directing the source to apply energy along a third path on the tissue, closer to the first path than to the second path, so as to ablate tissue therein.

Preferably, applying the energy along the first path includes placing a material on the tissue to increase the absorption into the tissue of energy applied by the source. Further preferably, the material includes a substance characterized by high absorbency of energy of a wavelength generated by the source.

In a preferred embodiment, the method includes actively cooling tissue in a vicinity of the first path. Preferably, actively cooling includes initiating the active cooling subsequent to ablation of the tissue in the first path. Alternatively or additionally, actively cooling includes applying a coolant in the vicinity of the first path. Further alternatively or additionally, actively cooling includes thermoelectrically cooling. Still further alternatively or additionally, actively cooling includes applying a cooled surface to the tissue in the vicinity of the first path. Typically, applying the cooled surface includes applying a cooled oscillating member to the tissue in the vicinity of the first path, which member is substantially not in contact with the tissue in the vicinity of the first path during a first phase of its oscillation and is in contact with the tissue in the vicinity of the first path during a second phase of its oscillation. Directing the electromagnetic energy source to apply energy along the first path on the tissue generally includes directing the source during the first phase.

In a preferred embodiment, the method includes applying a pharmaceutical product in a vicinity of the first path.

There is still further provided, in accordance with a preferred embodiment of the present invention, a method for applying energy to biological tissue, including:

placing a cover on the tissue; and directing a beam of electromagnetic energy through the cover to impinge on the tissue, so as to ablate a portion thereof.

Preferably, the cover includes a window, through which the energy beam passes.

Further preferably, placing the cover on the tissue reduces stimulation of nerves therein. Typically, placement of the cover defines a volume of an intermediate substance, between the cover and the tissue, and reducing stimulation includes maintaining a desired characteristic of the intermediate substance. The substance may include air and/or a liquid. In a preferred embodiment, the characteristic includes a temperature, a pressure, and/or humidity.

There is yet further provided, in accordance with a preferred embodiment of the present invention, a method for applying energy to biological tissue of a subject, including:

directing an electromagnetic energy source to apply the energy to a region of the tissue, so as to ablate a portion of the tissue in the region;

applying a liquid coolant to the tissue; and directing a flow of a gas towards the tissue, so as to increase a rate of evaporation of the liquid coolant.

Typically, the gas is directed to the tissue so as to reduce a perception of discomfort by the subject responsive to the coolant.

There is also provided, in accordance with a preferred embodiment of the present invention, apparatus for applying energy to biological tissue, including:

an electromagnetic energy source, directed to apply the energy to a region of the tissue, so as to ablate a portion of the tissue in the region; and a cooling unit, which initiates cooling of tissue in the region subsequent to the ablation.

In a preferred embodiment, the cooling unit includes a thermoelectric cooling unit.

Alternatively or additionally, the apparatus includes a pharmaceutical delivery unit, containing a pharmaceutical product for application to the tissue in a vicinity of the ablated portion.

Further alternatively or additionally, the apparatus includes a heating unit, which heats tissue cooled by the cooling unit, so as to decrease injury of the cooled tissue. Preferably, the apparatus includes a temperature sensor, which generates a signal responsive to a temperature of the tissue, wherein the heating unit heats the tissue responsive to the signal. In a preferred embodiment, the heating unit includes a thermoelectric element, through which element current is driven in a first direction so as to heat the tissue. Preferably, the cooling unit drives current through the thermoelectric element in a second direction so as to cool the tissue. Alternatively or additionally, the heating unit includes a heated surface which is applied to the tissue.

There is additionally provided, in accordance with a preferred embodiment of the present invention, apparatus for applying energy to biological tissue, including:

an electromagnetic energy source, which applies energy to the tissue; and a beam scanner, which directs the energy from the source along a plurality of paths on the tissue, including (a) a first path, so as to ablate tissue in the first path, (b) a second path, relatively distant from the first path, so as to ablate tissue in the second path, while allowing cooling of tissue adjacent to the first path heated by diffusion due to applying the energy to the first path, and (c) a third path, closer to the first path than to the second path, so as to ablate tissue in the third path.

There is yet additionally provided, in accordance with a preferred embodiment of the present invention, apparatus for applying energy to biological tissue, including:

a cover, placed on the tissue; and an electromagnetic energy source, which directs a beam of energy through the cover to impinge on the tissue, so as to ablate a portion thereof.

Preferably, the apparatus includes a pharmaceutical reservoir, containing a pharmaceutical product for application to the tissue.

There is also provided, in accordance with a preferred embodiment of the present invention, apparatus for applying energy to biological tissue of a subject, including:

an electromagnetic energy source, directed to apply the energy to a region of the tissue, so as to ablate a portion of the tissue in the region; and a cooling unit, which applies a liquid coolant to the tissue and directs a flow of a gas towards the tissue, so as to increase a rate of evaporation of the liquid coolant.

preferably, the cooling unit directs the gas to the tissue so as to reduce a perception of discomfort by the subject responsive to the coolant.

The present invention will be more fully understood from the following detailed description of the preferred embodiments thereof, taken together with the drawings, in which:

DETAILED DESCRIPTION OF PREFERRED EMBODIMENTS

Figure 1:
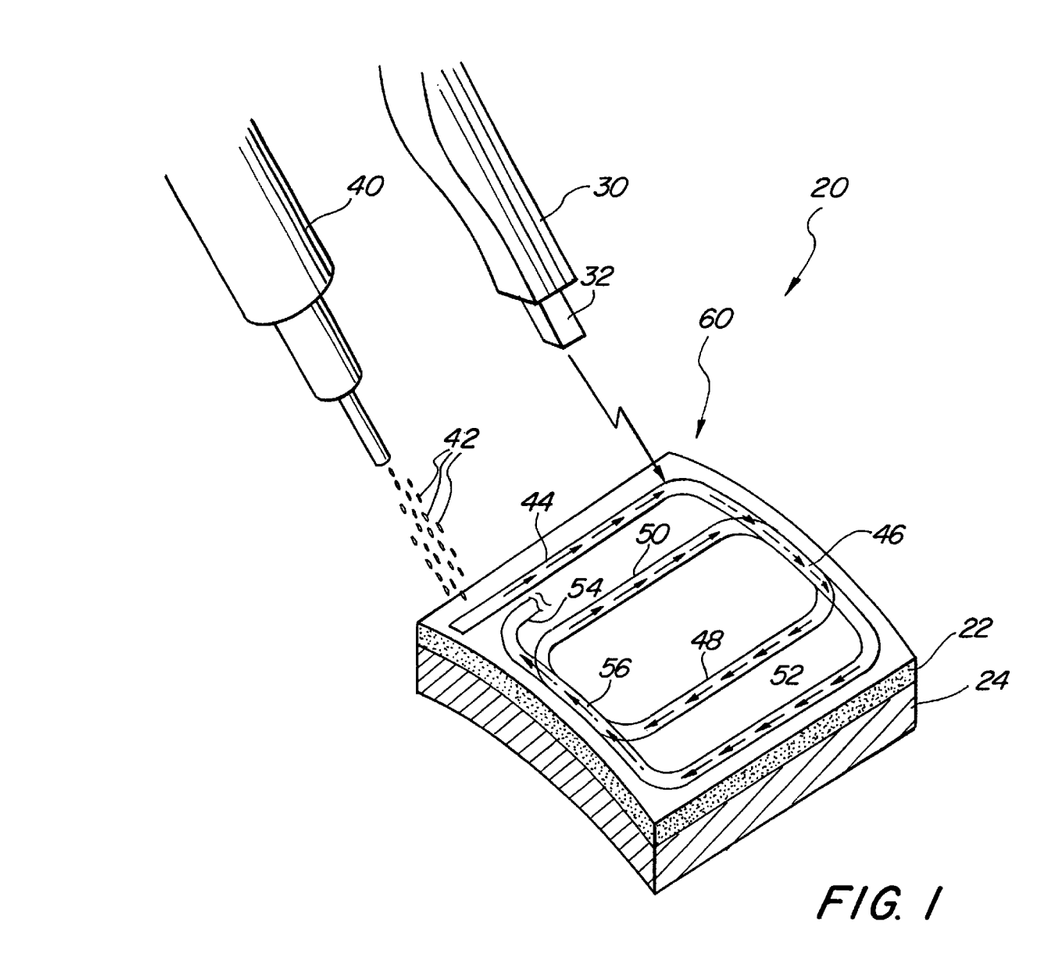
FIG. 1 is a simplified pictorial illustration of apparatus for ablating biological tissue, in accordance with a preferred embodiment of the present invention.

FIG. 1 is a simplified pictorial illustration showing apparatus 20 for ablating biological tissue, in accordance with a preferred embodiment of the present invention. Apparatus 20 comprises an electromagnetic energy source 30, which delivers energy to a target area 60 of a subject's skin 22, so as to ablate a layer of the skin from some or all of the target area. Thereafter, a cooling unit 40 removes some of the heat generated by the interaction of the energy with the target area, typically, but not necessarily, by applying a coolant 42 to the area, as described hereinbelow. Removal of the heat following the application of the energy generally reduces the subject's sensation of the heat, and, in particular, reduces any sensation of pain. Moreover, heat removal has been found to reduce or eliminate undesired injury to tissue surrounding the ablated area, or thereunder, such as underlying tissue 24. At least a substantial portion of the cooling generated by cooling unit 40 occurs following the application of the electromagnetic energy. It is believed that very rapid heating of a target area of the skin, substantially unmitigated by any prior cooling thereof, produces superior results relative to techniques which cool a mass of tissue and then apply energy to a cooled target area.

In a preferred embodiment, skin 22 comprises the subject's epidermis, and underlying tissue 24 comprises the dermis. In another preferred embodiment, skin 24 comprises the dermis, and underlying tissue 24 comprises the fat layer underlying the dermis.

In some preferred embodiments of the present invention, energy application and/or removal as described herein employs techniques such as are described in the above-cited PCT publication WO 98/55035 and in U.S. provisional patent application No. 60/111,436 entitled, "A method and apparatus for surgery and material processing," filed Dec. 8, 1998, which is assigned to the assignee of the present patent application. Both of these references are incorporated herein by reference.

It will be understood that whereas preferred embodiments of the present invention are described herein with respect to the ablation of an area of a subject's skin, for example, to treat skin lesions or wrinkles, it is within the scope of the present invention to apply the energy to other tissues or organs. Moreover, in other, non-biological biological applications of the present invention, the coordinated application and removal of energy from the target area preferably ablates some material while minimizing undesired damage to other material surrounding the ablation site. Thus, for example, in some applications of the present invention, silicon surfaces may be machined, hard and soft dental tissue may be ablated, metal products may be machined and shaped, or wood products may be precisely modified. Additionally, biomedical materials may be precisely processed prior to use.

Typically, but not necessarily, source 30 comprises a laser, for example, a Continuous Wave (CW) $CO_2$, Er:YAG, microchip, or diode laser, or a broadband emission lamp. Typically, source 30 transmits energy having a wavelength associated therewith ranging from about 200 nanometers to 15 microns, preferably from 300 nanometers to 2 microns. The energy generated by source 30 is preferably, but not necessarily, focused to a relatively small spot size, preferably between about 1 micron and 10 millimeters across, and further preferably between about 10 microns and 2 millimeters across. In a preferred embodiment, the spot is focused to between about 50 microns and 200 microns across. The average power imparted to target area 60 by source 30 is generally between 1 mW and 10 kW, typically between about 50 mW and 1 kW, and, in a preferred embodiment, from about 1 to 5 W.

In applications in which source 30 comprises a 10.6 micron CO2 laser, it has been found by the inventor that a low-power laser (e.g., 0.1–5.0 W) can be used effectively. This is believed to be a highly significant result, because a low-power CO2 laser is smaller, safer, and significantly less expensive than prior art lasers currently in use by dermatologists. Similarly, by applying the principles of the present invention, microchip and low-power diode lasers can be used in biological applications previously reserved only for much higher power lasers. It is further believed that by applying the principles and operating parameters as taught in some embodiments of the present invention, a system for applying energy to tissue—particularly a system for ablating tissue on or near the skin—can be constructed and operated by a person skilled in the art for significantly less money than is possible using materials and techniques which are known in the art. For example, it is believed that a low-power CO2 laser system with appropriate optics, cooling unit and control unit, which implements principles of the invention, could be constructed with parts which cost less than approximately $400 on Sep. 1, 1999 that are readily available from catalogs known in the art. The parts required to construct analogous systems that are commercially available, but do not implement these principles, generally cost at least $15,000.

In applications wherein low-power lasers or other energy sources are utilized, a high absorption substance (HAS) is typically applied to the skin to increase the efficiency of the energy transfer thereto. In experiments performed by the inventor, the HAS comprised India ink, which was applied to the skin prior to activation of a CO2 laser and was found to be effective at significantly increasing the absorption of energy in the skin. In a preferred embodiment, the HAS is characterized by some or all of the following properties:

- generation of heat and/or plasma responsive to energy application,
- energy absorption coefficient of at least 100/cm,
- biocompatibility,
- ease of application, as described hereinbelow,
- ease of removal, typically by washing with soap and water, and
- comprising an anti-oxidant, a disinfectant, a nutrient, an antibiotic, a pharmaceutical product to expedite healing, enhanced quantities of oxygen to expedite healing, and/or very small (e.g., 5 micron) energy-absorbing particles in solution.

The HAS is preferably applied to the skin, and, where applicable, given time to dry prior to activation of the energy source. Typically, the HAS is applied manually, e.g., by brush, pencil, tissue, or by rubbing in with the fingers. Alternatively or additionally, to enhance application speed, or when complex patterns are desired, an air brush, ink-jet, or other means of computer pattern generation may be used. In this manner, a high-resolution image can, for example, be applied by laser or other means to the skin.

In many of these applications, a high reflectance substance (HRS) is additionally or alternatively placed on the skin to inhibit application of the energy to certain regions of skin 22. Typically, application of the HRS reduces damage to sensitive areas on the skin and/or enhances the generation of a desired pattern. For example, HRS in combination with HAS can be used to produce a high-resolution image analogous to a tattoo.

Cooling unit 40 preferably removes a substantial portion of the applied energy shortly following the interaction thereof with target area 60. Typically, the cooling unit comprises an electronic coolant injector (analogous to an electronic fuel injector), which applies coolant 42 to the target area, such that the reduced temperature and/or evaporation of the coolant enhance the removal of energy from the target area. Depending on the particular application, coolant 42 may comprise a liquid, gas, gel, or a solid., e.g., a powder. Preferred coolants include chlorodifluoromethane (boiling point=–40° C.) and 1,1,1,2-tetrafluoroethane cryogenic spray (boiling point=–26° C.). It will be understood by one skilled in the art that many refrigerants are available that would be appropriate for cooling biological tissue following the application of energy thereto, as provided by embodiments of the present invention. Alternatively or additionally, cooling unit 40 cools target area 60 thermoelectrically, for example, as described hereinbelow with reference to FIGS. 2 and 3.

Preferably, cooling unit 40 is used to remove heat generated during a first interaction of energy with the target area in such a manner that the cooling substantially does not affect a subsequent interaction. Thus, for example, when coolant 42 comprises a liquid, the liquid preferably evaporates, and the temperature generally equilibrates prior to the next application of energy. Typically, after 5 ms of application of coolant 42 to an irradiated area, the temperature of the cooled area returns to approximately the pre-irradiation temperature within several tens of milliseconds.

Preferably, the coolant is applied for a period ranging from 0.1 ms to 1 second, typically for a period ranging from 0.5 ms to 10 ms. Further preferably, in order to avoid over-heating of tissue, coolant is applied after source 30 has released a pulse of energy having a duration of about 0.01 microseconds to 0.5 seconds. Still further preferably, timing of the application of coolant is determined responsive to a power setting of source 30.

In a preferred embodiment, cooling unit 40 releases compressed air onto a region where a liquid coolant landed, in order to increase the evaporation rate of the liquid. It has been observed by the inventor that use of compressed air to increase the evaporation rate may cause a transient decrease in temperature below that which would have occurred without the compressed air, but that this nevertheless appears to mitigate cold "burn," which may occur responsive to the application of a refrigerant to skin. A possible mechanism for the reduction of cold burn is the reduction of the time that the coolant sits on the subject's skin. The compressed air may comprise room temperature air, or, alternatively, warm or hot air, so as to further reduce cold burn. In some applications, when warm or hot air is used, areas around the target area are warmed, so as to still further reduce cold burn. This warming may comprise, for example, bringing a heating element into temporary contact with the cooled tissue following the cooling, so as to rapidly warm the cooled tissue. In a preferred embodiment, the element comprises a heating/cooling plate (comprising, for example, one of the cooling plates described hereinbelow with reference to FIG. 2). Preferably, the heating/cooling plate has respective heating and cooling phases thereof, in which, for example, thermoelectric cooling and heating, or cold and hot circulating fluids regulate the temperature of the plate.

Alternatively or additionally, source 30 warms the cooled tissue, typically transiently increasing the spot diameter generated by the energy source, so as to warm or heat, but not ablate, the tissue. Preferably, a temperature sensor is coupled to detect tissue temperature, and the heating/cooling plate is regulated responsive thereto.

For some applications, coolant 42 comprises a combination of a coolant, a nutrient, an oxygen-rich solution, and a pharmaceutical product, such as a topical anesthetic or an antibiotic, which is applied to the target area after the application of the energy, so as to enhance healing, and/or reduce pain and/or reduce a likelihood of infection or other injury responsive to the procedure. Alternatively or additionally, the aforementioned components of coolant 42 are administered independently of each other.

Preferably, the energy emitted by source 30 comprises a beam of energy, which is moved by a beam scanner 32 coupled to source 30 in a pattern over target area 60 designed to minimize the accumulation of heat in a vicinity of the target area, and thereby to reduce unnecessary pain and/or injury. Typically, the pattern is predetermined, such that in a first pass of the beam over the target area, a first line 44 on the target area is irradiated, ablating the directly-irradiated tissue as desired. Other tissue in a vicinity of the first line is indirectly heated. Following the first pass, the energy source is typically either turned off or prevented from transmitting to the target area, while the beam is re-directed along a non-irradiated path 46 to a new starting point, relatively remote from first line 44. Subsequently, a second line 48 is irradiated during a second pass, to achieve the desired ablation of directly-irradiated tissue. Although tissue in a vicinity of line 48 is typically heated indirectly during the second pass, the tissue in the vicinity of line 44 is preferably not heated in any substantial manner during the second pass. As a result, the temperature of this latter tissue generally decreases during the second pass. Typically, although not necessarily, cooling unit 40 operates to enhance the temperature decrease. Optimally, the temperature decreases to approximately the same temperature as prior to the first pass.

Preferably, scanner 32 directs the beam over target area 60 in a series of passes, which apply energy as necessary to ablate tissue, but minimize the undesired accumulation in nearby tissue of indirect heating. In a preferred embodiment, the energy from source 30 is applied to the skin in sets of passes, whereby a set of one or more consecutive passes across the skin is relatively distant from a preceding set of one or more consecutive passes. Utilization of a beam pattern as shown in FIG. 1, based on irradiation of lines 44, 48, 50, 52, and 54, linked by "beam-off" lines 46 and 56, minimizes the unnecessary accumulation of heat in particular regions of the tissue, and thus reduces injury and sensations of pain in non-targeted tissue. Optionally, cooling unit 40 removes energy from a given irradiated line during the "beam-off" period following the respective beam pass. Alternatively or additionally, the cooling unit operates on one part of a line while another part is being heated. Further alternatively or additionally, one line is heated while a previously-heated line is cooled. Still further alternatively or additionally, one or more lines are irradiated, after which unit 40 cools some or all of the target area.

By way of illustration and not limitation, a 10 W, 100 micron spot may be directed to pass along a 1 cm line in 10 ms, wherein its ablating energy is absorbed to an approximate depth of 10 microns. Thereafter, the beam is turned off or blocked, redirected to a point remote from the line just irradiated, and scanned across a second line. The redirection during the "beam-off" period may take an additional 10 ms. Thirty milliseconds following ablation of the first line, a third line is irradiated in close proximity thereto. In a typical cycle, ablative energy deposited in a small volume of tissue during a first pass will have diffused into a substantially larger volume of tissue prior to application of energy during a later pass to an area proximate to the tissue ablated during the first pass. The ratio of the large tissue volume to the small tissue volume, continuing with the illustrative parameters cited above, is typically 250:1. Ablation of a 1 cm×1 cm patch, using beam-scanning methods provided by the preferred embodiments of the present invention, would in this case typically take not more than several seconds. It may be desirable in some applications, however, to direct the beam to irradiate a previously-irradiated area, in order to ablate successively deeper layers of tissue.

Using preferred parameters, the area which is scanned in one second is between about 0.5 mm2 and about 3 cm2, typically, between about 1 mm2 and about 10 mm2 per second. Preferably, the depth of ablation during each pass is between 1 micron and 1 millimeter, typically between about 10 microns and about 70 microns.

Standard optical and electronic apparatus known in the art may be used to implement the beam-focusing and beam-scanning techniques utilized in some preferred embodiments of the present invention. For example, most of these embodiments have at least some of the following: optical fibers, hollow wave-guides, mirrors, lenses, electrical and opto-electronic components, motorized optical elements, electro-optical modulators, acousto-optical modulators, diffraction gratings, a function generator, and a microprocessor.

It will be appreciated that a straight-line, raster-style beam pattern is shown in FIG. 1 by way of example, and that the scope of the present invention includes substantially any pattern that allows the heating and cooling of different areas of the target area in rapid succession, as described hereinabove. For example, individual spots within the target area may be irradiated randomly. Alternatively, the beam may sweep out, in successive passes across the target area, the or more sine waves, wherein the ratio of the period of the sine waves to the width of the target area is selected so as to reduce accumulated heating.

It is generally preferable to apply energy at a high rate to tissue in the target area 60, in order to rapidly ablate the surface tissue, and to avoid slowly "cooking" a larger mass of non-targeted tissue. Thus, the dwell time of the beam over any point along lines 44, 48, 50, and 52 is preferably between about 1 picosecond and 300 milliseconds, further preferably between about 1 microsecond and 10 milliseconds, and, in some embodiments, most preferably between 100 microseconds and 1 millisecond.

Figure 2:
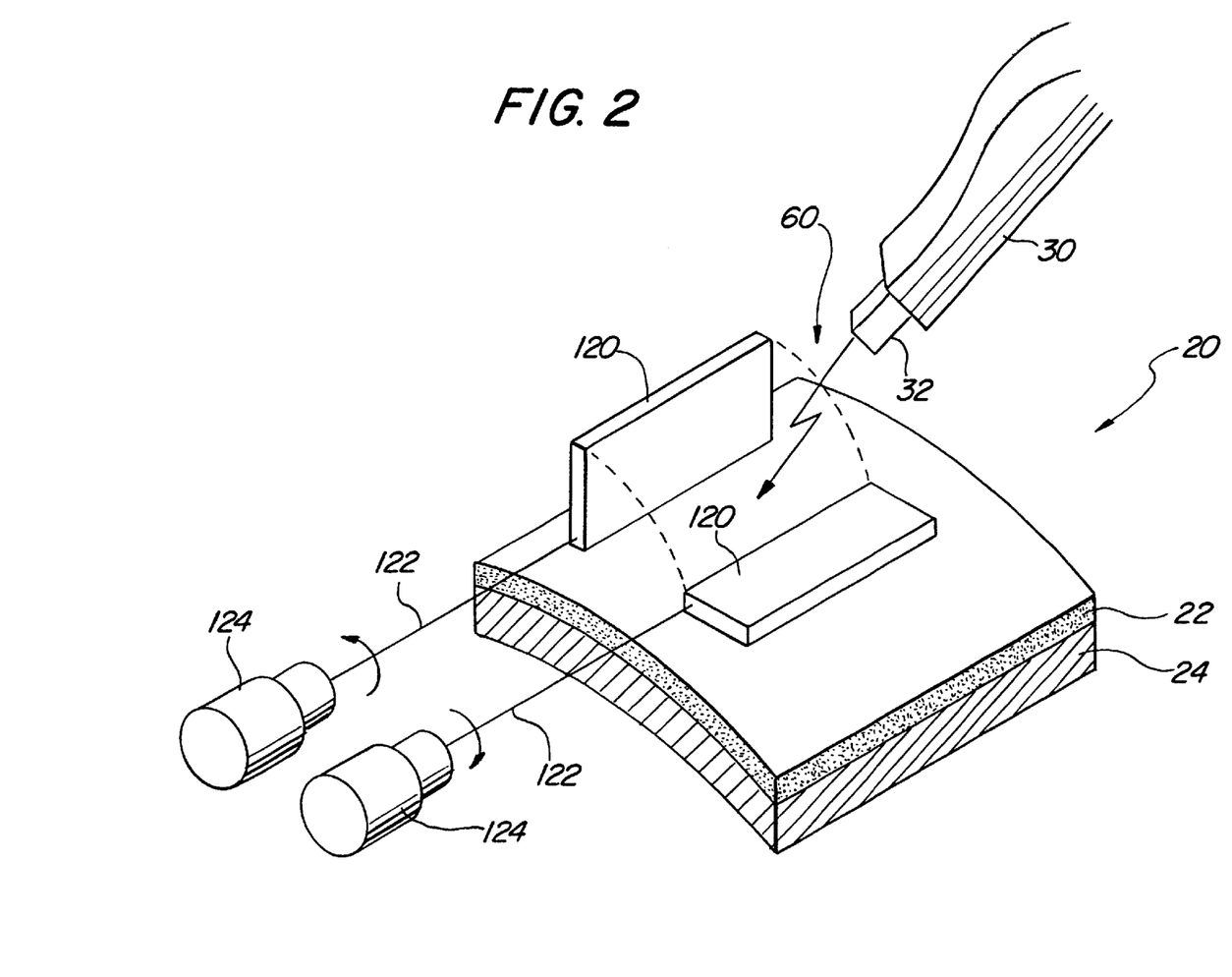
FIG. 2 is a simplified pictorial illustration of apparatus for ablating biological tissue, in accordance with another preferred embodiment of the present invention.

FIG. 2 is a simplified pictorial illustration of apparatus for ablating biological tissue, in accordance with another preferred embodiment of the present invention. The embodiment shown in FIG. 2 is generally similar to that described with reference to FIG. 1, differing substantially only in the manner of applying cooling to target area 60. Techniques as described hereinabove with respect to a beam pattern which inhibits excess accumulation of heat in the tissue may be used to particular advantage in this embodiment, as well. Preferably, at least one cooling plate 120 is placed on target area 60 prior to a procedure, and is in a first position when source 30 applies energy to the target area, and is moved to a second position following application of energy to the area. As shown in FIG. 2, during energy application to one region of target area 60, the nearest cooling plate 120 is moved by an actuating element 124 into an "up" position, so as to substantially not cool the area, while another one of the cooling plates is moved by another one of the actuating elements into a "down" position, to cool off a region of target area 60 which had recently had energy applied thereto.

In a preferred embodiment, elements 124 rotate cooling plates 120 between the respective positions, as shown. In another embodiment, elements 124 actuate cooling plates 120 to rapidly oscillate without rotation between a first position, touching the target area, and a second position, not touching the area. Preferably, appropriate parameters and properties of the actuating elements and the cooling plates are chosen such that the oscillation frequency of each plate corresponds to a frequency associated with the application of energy to the target area (e.g., pulse repetition rate or raster scan rate). In this and other embodiments, it is preferable but not necessary for the cooling plates to be substantially transparent to the wavelength(s) of energy source 30, so that the motion of the plates can be minimized without substantially compromising the application of energy to the target area.

Plates 120 may be cooled by appropriate methods known in the art. According to a preferred embodiment of the present invention, the plates are cooled thermoelectrically, with power supplied through a connecting member 122. Alternatively, a cooled fluid may be driven through member 122 into the cooling plates, either intermittently or throughout a procedure.

It will be appreciated that whereas two cooling plates are shown in FIG. 2, this is by way of example only, and in other applications of the present invention, one plate or a larger number of plates may be used.

Figure 3:
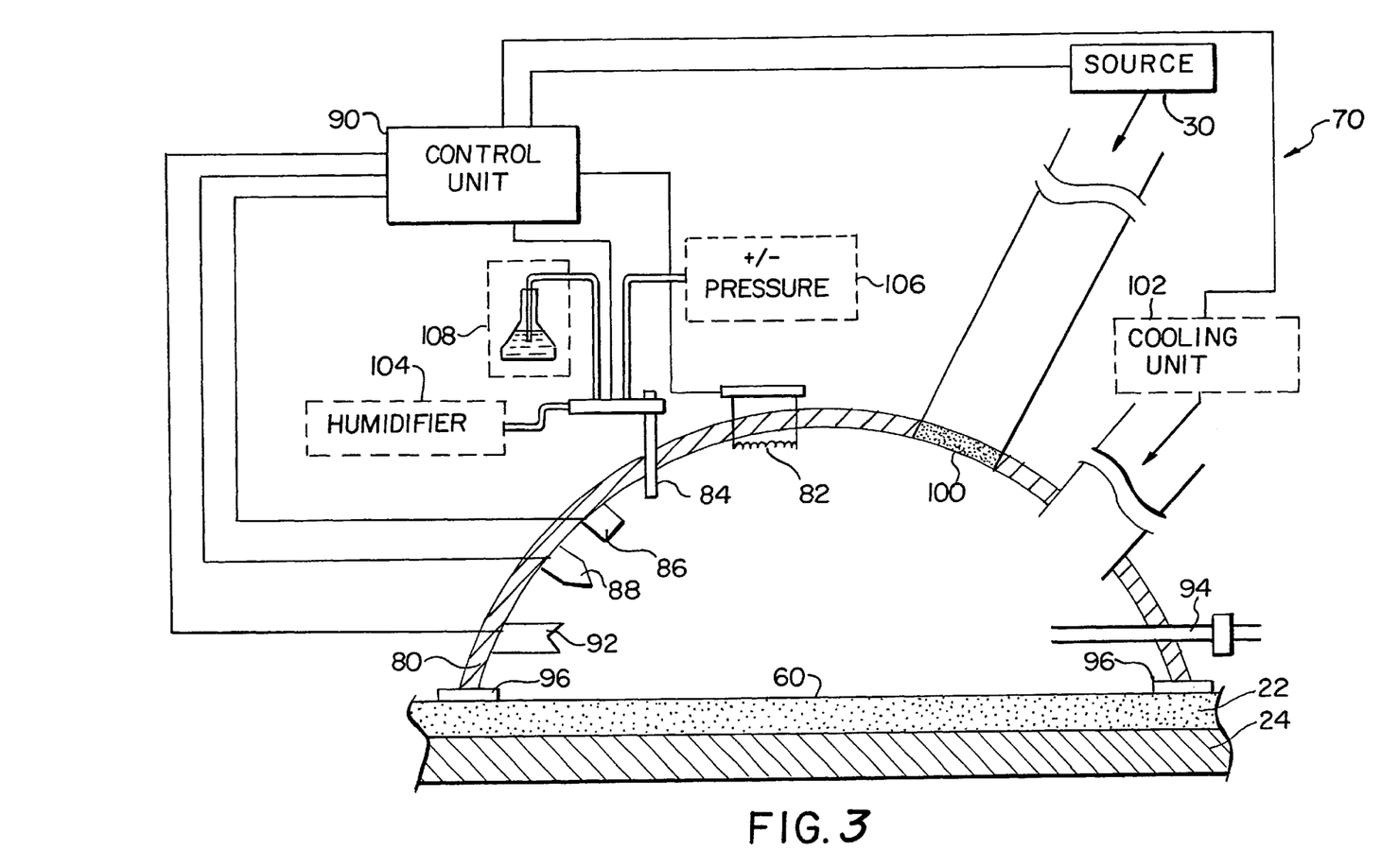
FIG. 3 is a schematic, sectional view of apparatus for ablating biological tissue, in accordance with yet another preferred embodiment of the present invention.

FIG. 3 is a schematic sectional view of apparatus 70 for ablating tissue in target area 60, while minimizing pain and collateral injury, in accordance with another preferred embodiment of the present invention. Elements of apparatus 70 may be used to ablate tissue in conjunction with or separately from apparatus 20, described hereinabove with reference to FIG. 1.

It is believed that stimulation, such as changes in temperature, of certain neurons may be associated with a pain sensation, and it is thus an object of the embodiment shown in FIG. 3 to minimize the pain sensation by reducing the number of unnecessary inputs to innervated tissue affected by the energy generated by source 30. Therefore, the temperature and other environmental parameters near target area 60 are controlled, as described hereinbelow.

Preferably, a cover 80 is placed over target area 60, and source 30 conveys electromagnetic energy to the target area through a window 100 in the cover. Window 100 is preferably substantially transparent to the wavelength(s) generated by source 30, and comprises, for example, zinc selenide to pass 10.6 micron radiation, or fused silica to pass visible light or near ultraviolet or near infrared radiation.

Cover 80 preferably enables an operator to maintain over the target area an ambient environment having properties, such as temperature, pressure, and humidity, which are set so as to minimize pain or discomfort during a procedure. Typically, temperature, pressure, and supplemental sensors 86, 88, and 92, are coupled to the cover in order to determine respective parameters of the ambient environment and to generate sensor signals responsive thereto. Supplemental sensors 92 may comprise, for example, a spectrometer, an infrared temperature sensor, a thermocouple, a moisture sensor, and/or an optical fiber collector or emitter for optical coherent tomography. A control unit 90 is coupled to receive the signals and to actuate various devices so as to cause the signals to converge to desired values. The actuated devices may include, for example, a heating element 82, an optional cooling unit 102, a gas and material transfer valve 84, and a controlled smoke-evacuating valve 94.

Preferably, a base ring 96 of cover 80 sits comfortably on skin 22, and provides a generally air-tight seal. The seal is optionally enhanced by prior application of a petroleum-based or other viscous substance, and/or by generating a low-level of negative air pressure under cover 80.

Cooling unit 102 preferably comprises a thermoelectric cooling element and/or cooling apparatus such as that described hereinabove with respect to cooling unit 40. In some applications, cooling unit 102 and heating element. 82 are parts of one integrated assembly, and heating or cooling of the environment above target area 60 is controlled by regulating the direction and magnitude of current to the assembly.

In a preferred embodiment, multiple cooling units 102 are located in a vicinity of target area 60 (e.g., in a square array over the area or circumferentially disposed thereabout), typically in contact with or a small distance above the target area. Preferably, control unit 90 actuates source 30 to irradiate a portion of the target area, and, shortly thereafter, actuates the cooling unit in closest proximity to the heated area. Each actuated cooling unit cools the heated area in its proximity, typically by one or more of the following:

releasing cooled particles toward the desired area (as shown in FIG. 1), applying a cooled surface to the skin, the surface preferably being thermoelectrically cooled or having a cooled fluid pumped through channels therein, or applying a cooled oscillating member to the skin (e.g., as shown in FIG. 2), the oscillation most preferably having a frequency determined in accordance with a pulse repetition frequency of source 30, such that the member is in contact with the target area substantially only at times when energy is not being applied thereto by source 30.

Although preferred embodiments of the present invention are described with respect to applying cooling only to regions that were recently irradiated by source 30, it will nevertheless be appreciated that it is within the scope of the present invention to use a simpler cooling apparatus, which cools part or all of target area 60 shortly before or after substantially each pulse or set of pulses generated by source 30, generally regardless of the precise irradiation location.

Gas and material transfer valve 84 preferably controls the flow of one or more substances into and out of cover 80. For example, the humidity and pressure under cover 80 are controlled, as appropriate, by an optional pressure source 106 and humidity controller 104. Alternatively or additionally, a nutrient, an oxygen-rich solution, or an optional pharmaceutical product 108, for example, a topical anesthetic and/or an antibiotic, is administered through valve 84 in conjunction with the application of electromagnetic energy to skin 22. Further alternatively or additionally, valve 84 regulates at the beginning of a procedure or in real-time throughout the procedure a gas and/or liquid composition between cover 80 and target area 60. By way of illustration and not limitation, the composition may comprise (a) inert gases, such as nitrogen or helium, (b) oxygen-enriched air, (c) oxygen and another gas, (d) a saline solution, or (e) distilled sterile water.

The energy from source 30 is preferably focused to a spot in target area 60 approximately 5 microns–5 millimeters in diameter, most preferably between about 10 and 300 microns. As described with reference to FIG. 1, the spot is preferably moved according to a predetermined pattern across target area 60. Preferably, any given point in the target area is illuminated by source 30 for between 1 nanosecond and 100 milliseconds, most preferably between about 1 microsecond and 1 millisecond.

Figure 4:
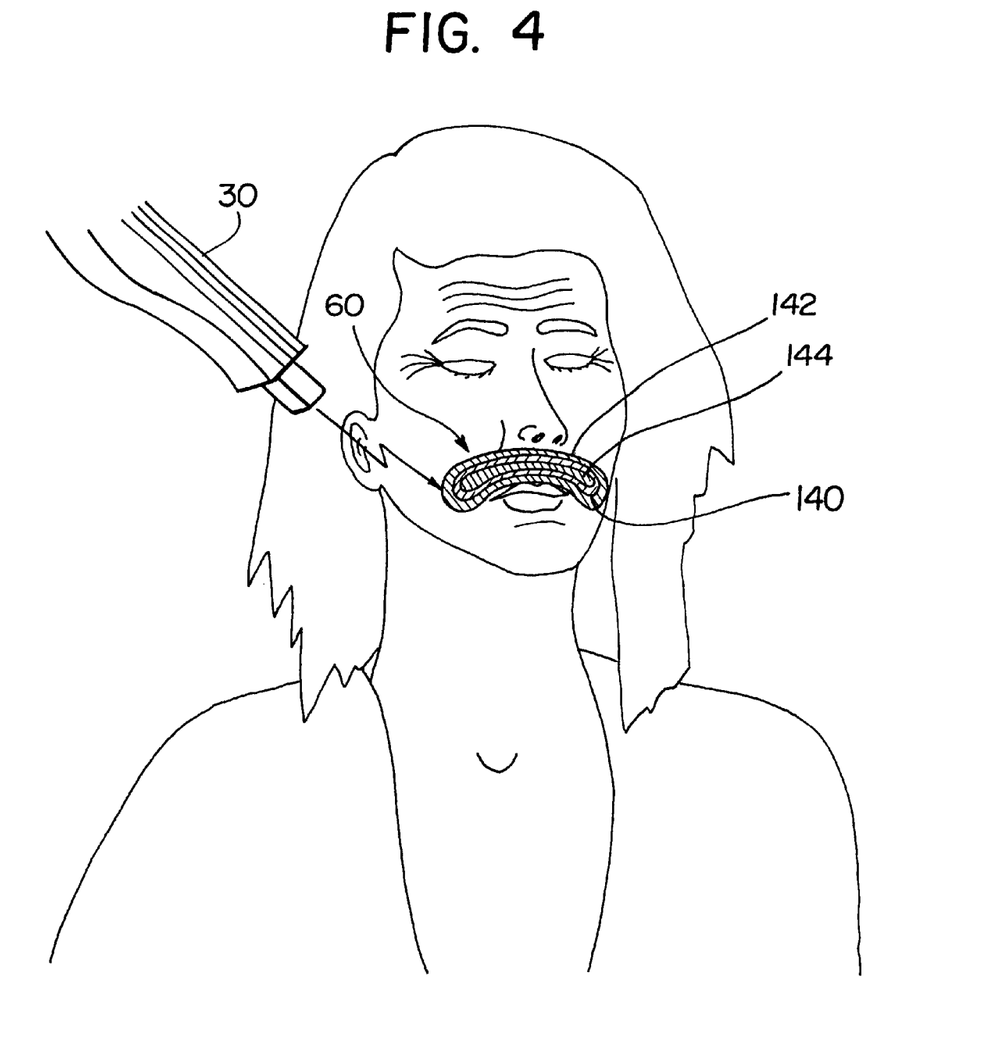
FIG. 4 is a simplified pictorial illustration of apparatus for ablating biological tissue, in accordance with a preferred embodiment of the present invention.

FIG. 4 is a simplified pictorial illustration, showing an ablation "tapering" method, typically but not necessarily employing some of the apparatus and techniques described hereinabove, in accordance with a preferred embodiment of the present invention. Target area 60 comprises an inner zone 144, an outer zone 140, and one or more optional intermediate zones 142, located between the inner and outer zones. Preferably, the greatest quantity of energy per unit area is absorbed in zone 144, and a gradual tapering off of the energy absorption is achieved in intermediate zone(s) 142 and in outer zone 140. Typically, the tapering process, as provided by these embodiments of the present invention, removes the sharp, visibly-noticeable delineation between a treated zone and an untreated zone, which is commonly produced by similar methods known in the art.

Using methods described herein, ablation thicknesses as small as approximately 8 microns per pass can be reproducibly achieved, which is sufficiently small to give an operator of the apparatus the ability to ablate to a depth of, for example, several hundred microns in inner zone 144, and to taper the ablation depth down, in successive intermediate zones 142, until outer zone 140 is ablated to a depth of only 10 microns. Standard high-power CO2 lasers typically used in dermatological treatments, by contrast, can not produce an ablation depth of less than approximately 100–200 microns, and therefore do not enable the operator to achieve the tissue "sculpting," as provided by preferred embodiments of the present invention.

Figure 5:
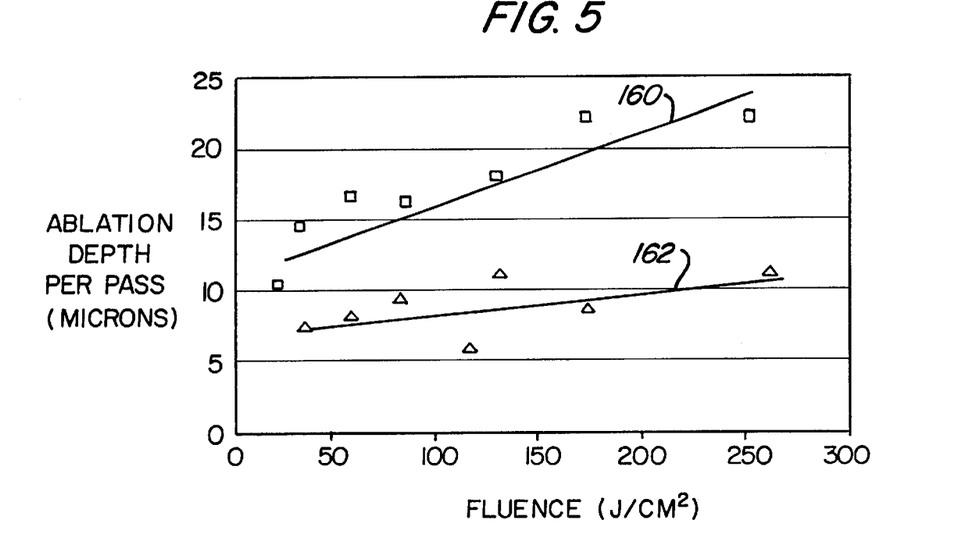
FIGS. 5–8 are graphs, showing results obtained from experiments with biological tissue, in accordance with a preferred embodiment of the present invention.

FIG. 5 is a graph showing experimental results obtained using some of the apparatus and methods described hereinabove, in accordance with a preferred embodiment of the present invention. In this experiment, beam scanner 32 produced a raster pattern of a 200 micron diameter spot on multiple patches of 5.3×7.3 mm cadaveric pig skin. Source 30 comprised a 1 W continuous wave 808 nm laser diode manufactured by Polaroid Corp. (Cambridge, Mass.), which is sold for $350. The fluence of energy applied to the patches ranged from about 25–260 J/cm2. A high absorption substance comprising drawing ink #4465, produced by Eberhard Faber, Inc. (Lewisburg, Tenn.), and/or Microna matte black cosmetic pigments, produced by EM Industries (Dermstadt, Germany), was applied to each patch.

Twelve complete passes of the beam over the entire target area were executed for each skin patch. During each pass, beam scanner 32 made the spot trace a generally sinusoidal pattern starting at one end of the target area, and ending at the other end of the target area, such that the 200 micron spot was directed at substantially every location in the target area at some time during the pass. The sinusoidal pattern had a frequency of 5 Hz, and each of the twelve passes started approximately 2 seconds following the start of the previous pass. In other experiments (not shown), these values have ranged from 2 Hz, starting a new pass every 5 seconds, to 50 Hz, starting a new pass five times a second.

Two experimental groups were created: (i) a cooled group, in which coolant was applied to the entire patch after each of the twelve passes (n=7), and (ii) a non-cooled group, which was not cooled between passes (n=7). Following the experiment, each skin patch was analyzed under a microscope to determine the average ablation depth per pass, i.e., the total ablation depth divided by twelve. The cooled group, as represented by triangles and an exemplary line 162 in FIG. 5, displayed consistently lower ablation than did the non-cooled group, represented by squares and an exemplary line 160.

Figure 6:
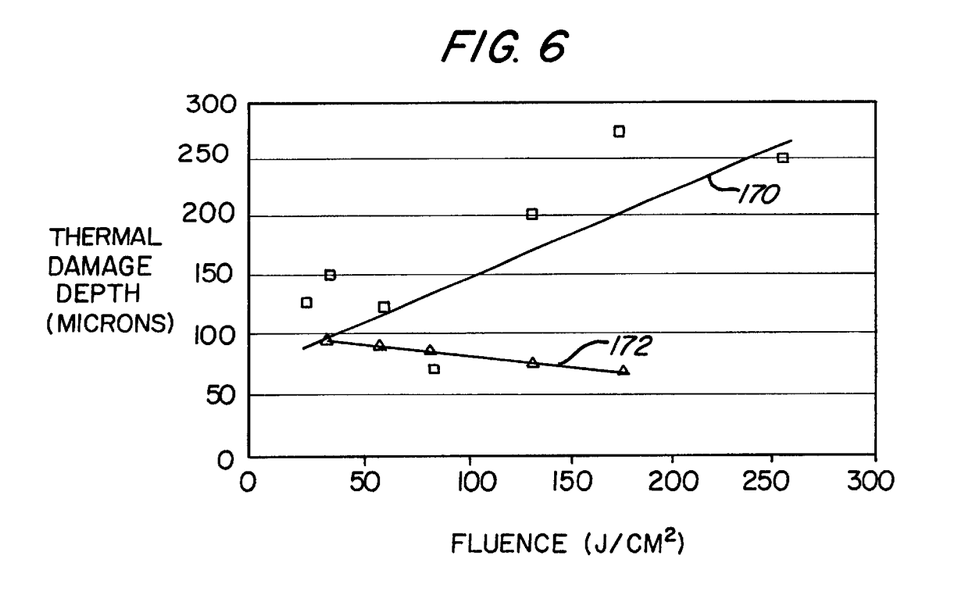

FIG. 6 is a graph showing other experimental results obtained using some of the apparatus and methods described hereinabove, in accordance with a preferred embodiment of the present invention. The data shown in FIG. 6 were obtained by making measurements from the same skin samples described with reference to FIG. 5, after the application of the energy thereto.

Typically, energy application to biological tissue, as taught by embodiments of the present invention, ablates tissue down to a certain depth, and causes thermal damage without ablation to tissue below the ablated region. In this experiment, the depth of thermal damage was determined using microscopic analysis, and the cooled group, represented by triangles and an exemplary line 172, displayed thermal damage at shallower depths (75–100 microns) than did the non-cooled group (80–275 microns), represented by squares and an exemplary line 170. It is additionally noted that, in contrast to the non-cooled group, the cooled group did not show increasing thermal damage depth with increasing fluence.

Figure 7:
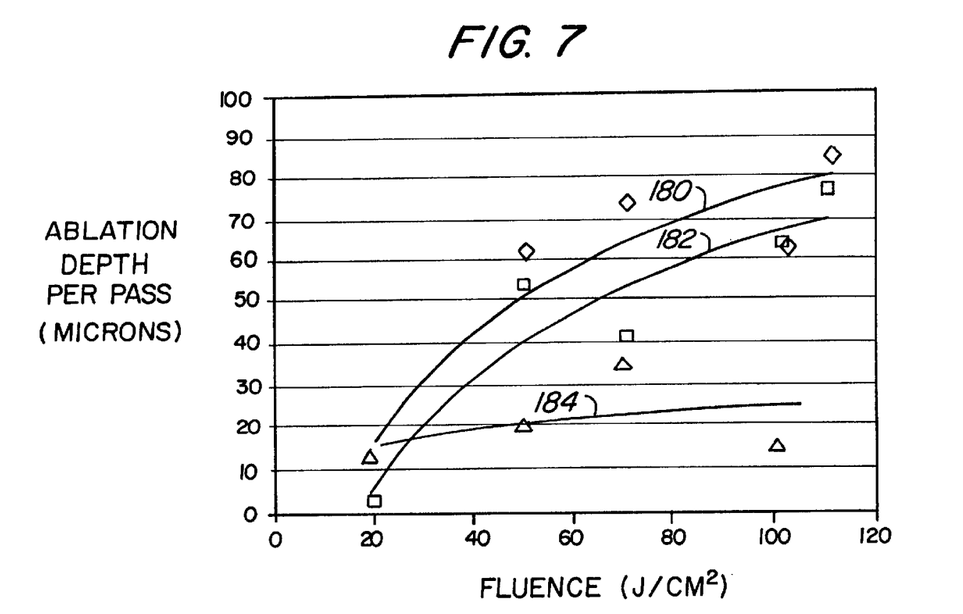

FIG. 7 is a graph showing still other experimental results obtained using some of the apparatus and methods described hereinabove, in accordance with a preferred embodiment of the present invention. Experimental parameters were generally as described hereinabove with reference to FIGS. 5 and 6, except as noted.

In this experiment, a 100 micron spot was scanned across a set of 3.5×3.0 mm cadaveric pig skin patches. Each patch was pre-assigned to one of three groups: (i) a group in which beam scanner 32 executed 2 passes, this group being represented in the figure by diamonds and an exemplary line 180, (ii) a 4-pass group, represented by squares and an exemplary line 182, and (iii) a 10-pass group, represented by triangles and an exemplary line 184. For each group, the average ablation depth per pass was measured as a function of the applied energy fluence. Generally, it is seen that the average ablation depth per pass is highest in the 2-pass group, lower in the 4-pass group, and lowest in the 10-pass group. It is believed that this results from gradual destruction in each pass of the high absorption substance applied prior to the experiment, yielding low per-pass energy absorption in the later passes. For some applications of these embodiments of the present invention, this is advantageous, while in other applications, an operator might intermittently re-apply the high absorption substance. In a preferred embodiment, the high absorption substance is mixed with, or applied simultaneously with the coolant.

Figure 8:
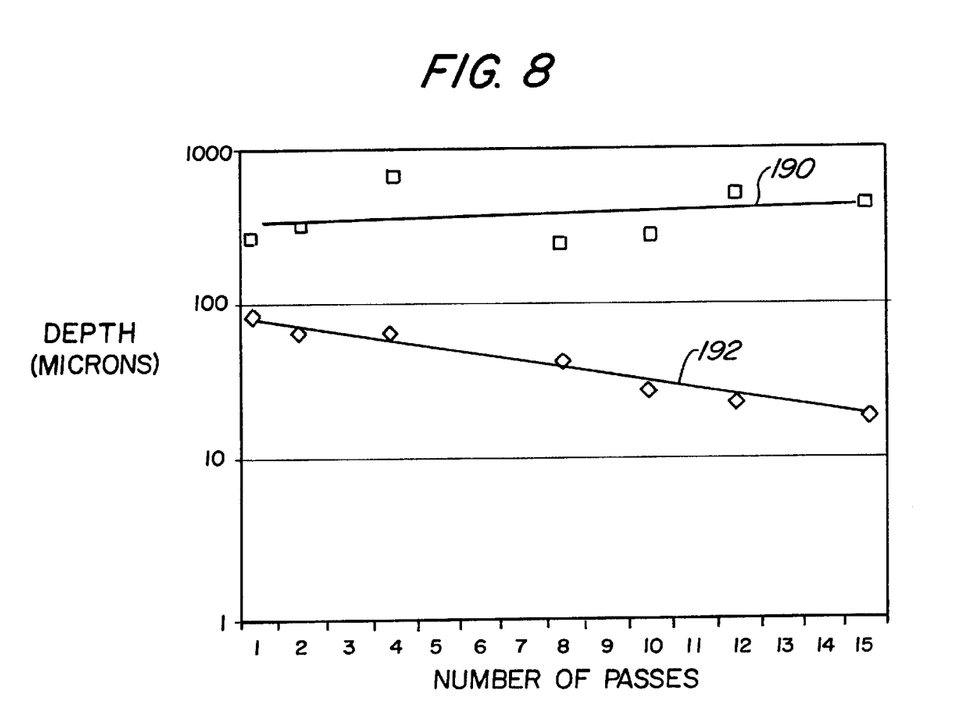

FIG. 8 is a graph showing yet other experimental results obtained using some of the apparatus and methods described hereinabove, in accordance with a preferred embodiment of the present invention. Experimental parameters were generally as described hereinabove with reference to FIG. 7, except as noted. Measurements of average ablation depth per pass and total (not average) thermal damage depth were made for a fixed fluence of 50 J/cm2, on skin samples which were exposed to differing numbers of passes. FIG. 8 shows that the total thermal damage below the ablated region, represented by squares and an exemplary line 190, had no tendency to increase or decrease, irrespective of the number of passes. Average ablation depth, represented by diamonds and an exemplary line 192, decreased with increasing numbers of passes.

FIGS. 5–8 demonstrate that using principles taught herein, it is possible to select parameters that control the depth of tissue ablation as well as the depth of thermal damage in skin underlying the ablated region. In particular, average ablation depths per pass as low as 8 microns were achieved, which may be of use in applying the tapering method described hereinabove with reference to FIG. 4.

In some preferred embodiments of the present invention (not shown), some of the energy application, cooling, and other methods and apparatus described hereinabove are used to enhance transdermal drug or nutrient delivery. In particular, transdermal drug delivery may be enhanced by causing rapid expansion of holes in the skin, for example, pre-existing pores, through which the drug is caused to pass. Preferably, but not necessarily, cooling unit 40 comprises a pharmaceutical delivery unit which delivers a pharmaceutical product before or after delivery of coolant 42. Alternatively, coolant 42 comprises the pharmaceutical product. Further alternatively or additionally, the pharmaceutical delivery unit is a separate unit from the cooling unit. Similarly, acne may be treated or prevented through pore-expansion. In a preferred embodiment, a HAS as described is applied to skin pores to enhance the deposition of energy therein. An exemplary set of energy-application parameters for acne treatment, drug delivery, or other procedures, is the application of 100 mW for 1 ms, i.e., 0.1 mJ.

In further preferred embodiments of the present invention a method and an apparatus for teeth whitening and removing unwanted blemishes and unwanted color from hard dental tissue can be envisioned. These methods and apparatus can be better understood with the aid of FIG. 9. A light source 200 of up to several tens of watts in power is used. The light source is coupled to a fiber bundle 202 consisting of several individual fibers 204.

Figure 9:
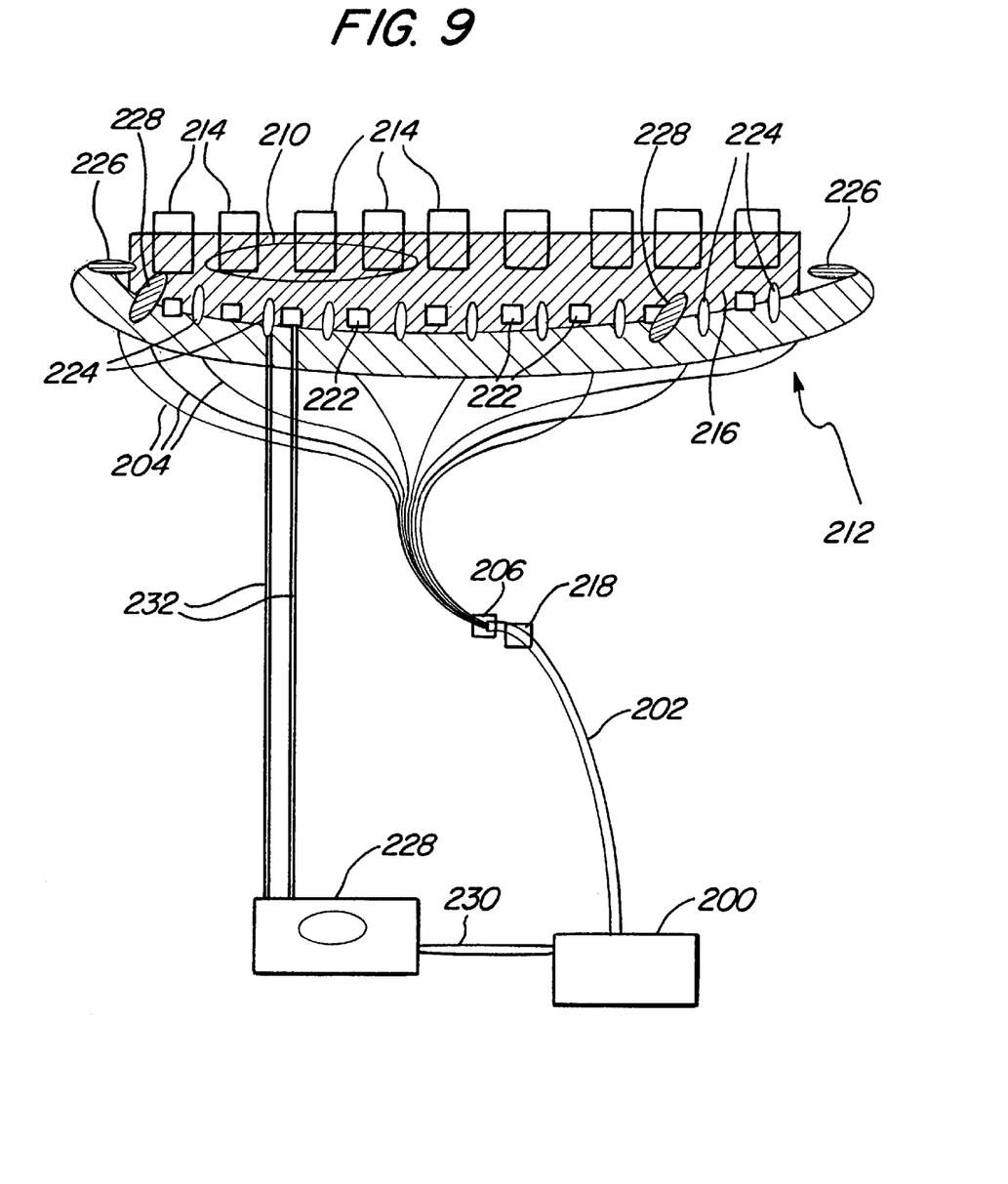
FIG. 9 is a simplified pictorial illustration of apparatus for achieving tooth whitening and the removal of unwanted colors and unwanted blemishes from hard dental tissue, in accordance with a preferred embodiment of the present invention.

A fiber separator 206 positioned in the fiber bundle in the vicinity of the coupler allowing the fibers of the fiber bundle to be separated into individual fibers so that each fiber delivers its light to a different portion of the upper or lower jaw, and thus to different set of teeth (for example, regions 208 and 210).

A coupler 212 that fit snag over the entire set of teeth 214 (either upper or lower set of teeth or both). The coupler is coated with a highly reflective substance 216 on its outer surface so that substantially much of the light within the coupler is not lost but is confined to the interior of the coupler, allowing repeated interaction with the teeth.

A tilt adjustment 218 on the coupler allowing varying the position of the coupler with respect to the teeth, thus allowing the coupler to be attached at varying angles with respect to the teeth and allowing the beam regions with the highest intensity to be directed at the teeth at varying angles and impinge on the teeth at varying locations, The Light source trigger 220 allows the operator to activate the source for time duration sufficiently long to achieve activation of a bleaching agent or for time duration sufficiently long for direct interaction eliminating unwanted color and unwanted blemishes to be completed. If necessary a repeated activation can be affected.

Additionally, a sensor or several sensors 222 (for example, optical sensor 222 or thermal sensors 224) connected to a computer control 228 (for example via cables 232, or in a wireless fasion) can be positioned with the coupler to monitor the effectiveness of the treatment and thus, automatically, using a feedback 230, reactivate the light source for longer or repeated treatment. One such envisioned sensor may be a photodiode. If the treatment if effective less light will be absorbed by the teeth and the output signal of the photodiode will increase. Another envisioned sensor may be a spectrometer capable of measuring changes in the absorption and reflection of specific spectral line corresponding to changes in the concentration of unwanted absorber (for example color centers) in the teeth.

The feedback can also affect increase or decrease in light source 200 power, or in response to thermal sensors 224 measurements, may initiate a cooling from a coolant dispenser 226, or may dispense, for example, a bleaching agent, medication or anaesthetic from a dispenser 228.

Figure 10:
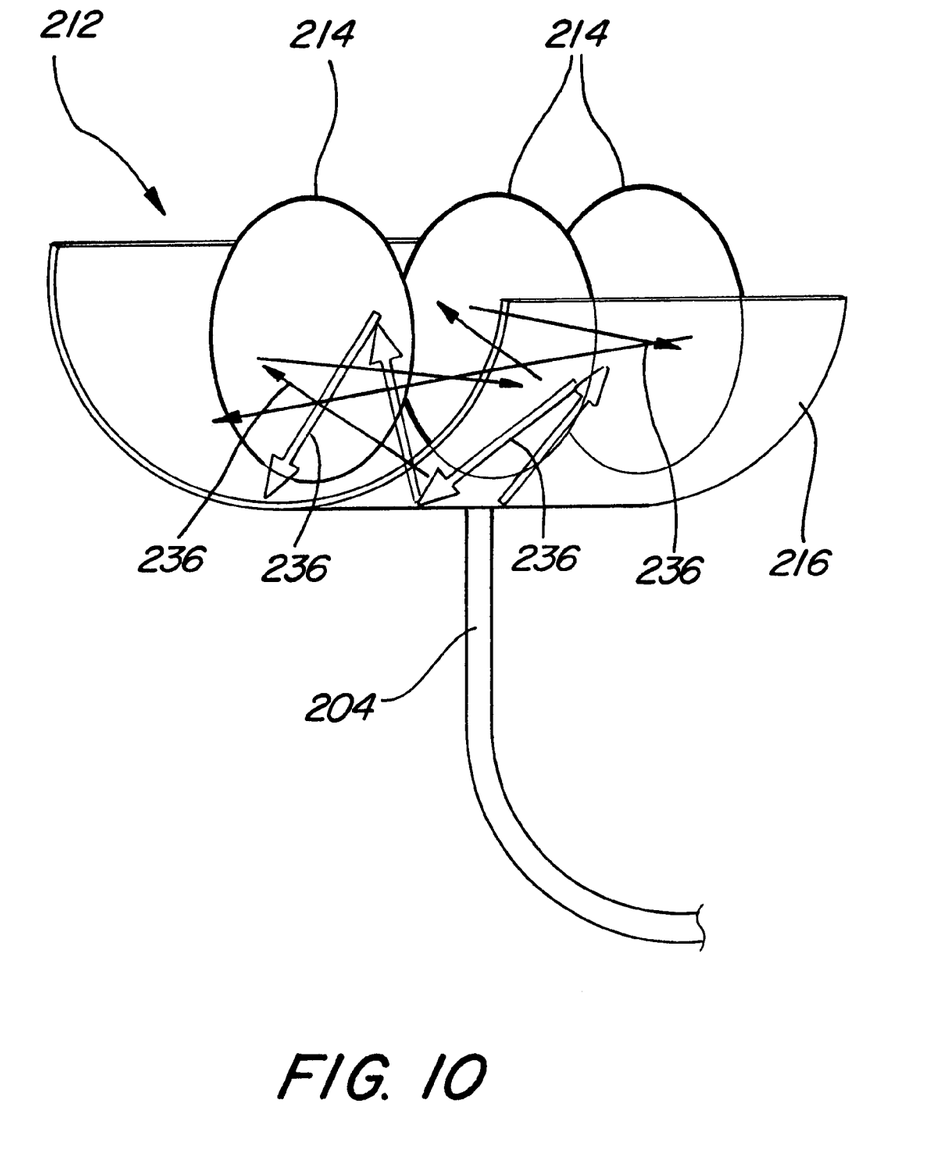
FIG. 10 is a simplified pictorial illustration of the way the photons from an optical fiber emitted within the dental coupler, will undergo multiple reflection to enhance their action on unwanted color centers, pigments, and bleaching agents in the treated teeth.

FIG. 10 illustrate the principle of multiple reflection and multiple use of light energy within the coupler 212. Light photons 236 from an optical fiber 204 emerge and either impinge on the teeth 214 or encounter the substance of high reflectance on the walls of the coupler container 216. The photons 236 are then reflected back and ultimately will encounter hard dental tissue of the teeth 214. Multiple passes will ultimately result in absorption of a large number of photons within the unwanted color centers and unwanted pigments within the teeth and by the bleaching agents (if those are present). The heating followed by the absorption process will result in elimination of the unwanted color. Color-free hard dental tissue absorbs very little photons and hence will likely allow multiple pass of the photons.

It will be appreciated that although preferred embodiments of the present invention are described with respect to the application of energy to skin and the cooling of skin, typically for purposes such as treatment or removal of skin lesions or wrinkles, it is within the scope of the present invention to apply energy to and cool substantially any type of biological tissue. For example, tumors, polyps, hemangiomas, ectasias, arterio-venous malformations, esophageal varices, coronary arteries, hemorrhoids and cellulite deposits are appropriate sites for application of the principles of the present invention. Additionally, non-biological materials may be processed in accordance with some embodiments of the present invention, as described hereinabove. It will be further appreciated that, although preferred embodiments of the present invention are described herein with respect to an electromagnetic energy source, other heating devices are suitable in many applications. For example, these other heating devices may include an ultrasound energy source or a heating element which is placed in contact with the target area.

It will be understood by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

What is claimed is:

1. A method for applying energy to biological tissue, comprising:
   directing an electromagnetic energy source to apply the energy to a region of the tissue to ablate a portion of the tissue; and
   applying a cooled surface to the tissue by applying a cooled oscillating member to the tissue, the member being in contact with the tissue during one phase of its oscillation and not in contact with the tissue during another phase of its oscillation.

2. A method for applying energy to biological tissue, comprising:
   directing an electromagnetic energy source to apply energy to a region of the tissue to ablate a portion of the tissue;
   initiating cooling of the tissue in the region subsequent to ablation; and
   warming cooled tissue by directing the energy source to apply additional energy to the cooled tissue by enlarging a beam diameter of the energy source from a first diameter, used for ablating tissue, to a second diameter, used for warming tissue.

3. Apparatus for applying energy to biological tissue, comprising:
   an electromagnetic energy source for applying energy to a region of the tissue to ablate a portion of the tissue; and
   a cooling unit having a cooled surface on an oscillating member in contact with the tissue during one phase of its oscillation and not in contact with the tissue during another phase of its oscillation.

4. Apparatus for applying energy to biological tissue, comprising:
   an electromagnetic energy source for applying energy to a region of the tissue to ablate a portion of the tissue;
   a cooling unit for cooling tissue in the region; and
   a heating unit for heating tissue comprising a thermoelectric element through which current is driven in a first direction to heat the tissue and wherein the cooling unit drives current through the thermoelectric element in a second direction to cool the tissue.

5. Apparatus for applying energy to biological tissue, comprising:
   an electromagnetic energy source to apply the energy to a region of the tissue to ablate a portion of the tissue;
   a cooling unit to cool the tissue in the region subsequent to ablation; and
   a heating unit to heat the tissue cooled by the cooling unit by actuating the energy source to apply additional energy by enlarging a beam diameter of the energy source from a first diameter used for ablating tissue to a second diameter used for heating tissue.

* * * * *